US010945748B2

(12) United States Patent
Robert

(10) Patent No.: US 10,945,748 B2
(45) Date of Patent: Mar. 16, 2021

(54) END EFFECTOR APPARATUS FOR A SURGICAL INSTRUMENT

(71) Applicant: TITAN MEDICAL INC., Toronto (CA)

(72) Inventor: Rene Robert, East Greenwich, RI (US)

(73) Assignee: TITAN MEDICAL INC., Toronto (CA)

( * ) Notice: Subject to any disclaimer, the term of this patent is extended or adjusted under 35 U.S.C. 154(b) by 52 days.

(21) Appl. No.: 15/566,525

(22) PCT Filed: Feb. 29, 2016

(86) PCT No.: PCT/CA2016/000059
§ 371 (c)(1),
(2) Date: Oct. 13, 2017

(87) PCT Pub. No.: WO2016/165004
PCT Pub. Date: Oct. 20, 2016

(65) Prior Publication Data
US 2018/0098780 A1 Apr. 12, 2018

Related U.S. Application Data

(60) Provisional application No. 62/147,302, filed on Apr. 14, 2015.

(51) Int. Cl.
*A61B 17/29* (2006.01)
*A61B 18/14* (2006.01)
(Continued)

(52) U.S. Cl.
CPC .......... *A61B 17/29* (2013.01); *A61B 18/1445* (2013.01); *A61B 34/30* (2016.02);
(Continued)

(58) Field of Classification Search
CPC .... A61B 2017/2919; A61B 2017/2939; A61B 2017/292; A61B 2017/294;
(Continued)

(56) References Cited

U.S. PATENT DOCUMENTS 4,038,987 A * 8/1977 Komiya ............... A61B 17/122
606/142
5,312,434 A 5/1994 Crainich
(Continued)

FOREIGN PATENT DOCUMENTS

WO WO 2010/124129 10/2010

OTHER PUBLICATIONS

International Search Report and Written Opinion in PCT Application PCT/CA2016/000059, dated Apr. 1, 2016 in 8 pages.

*Primary Examiner* — Linda C Dvorak
*Assistant Examiner* — Ryan T Clark

(57) ABSTRACT

An end effector apparatus for a surgical instrument is disclosed. The apparatus includes a first jaw mounted on a first revolute joint, the first jaw having a manipulating portion extending forwardly from the first revolute joint and a lever arm projecting rearwardly from the first revolute joint. The apparatus also includes a second jaw having a manipulating portion generally opposing the manipulating portion of the first jaw, and a coupler having an actuation end disposed overlapping the lever arm of the first jaw, the first and second jaws being laterally spaced apart to provide clearance for the actuation end of the coupler. The apparatus further includes a linkage extending rearwardly between the actuation end of the coupler and the lever arm of the first jaw, the linkage being operable to cause opening and closing movements of the first jaw about the first revolute joint in response to reciprocating movement of the coupler.

20 Claims, 4 Drawing Sheets

(51) Int. Cl.
  *A61B 34/30* (2016.01)
  *A61B 17/062* (2006.01)
  *A61B 17/00* (2006.01)
(52) U.S. Cl.
  CPC ... *A61B 17/062* (2013.01); *A61B 2017/00473* (2013.01); *A61B 2017/2939* (2013.01)
(58) Field of Classification Search
  CPC .......... A61B 2017/2915; A61B 17/282; A61B 2017/00473; A61B 2017/2926
  See application file for complete search history.

(56) References Cited

U.S. PATENT DOCUMENTS

| | | | | |
|---|---|---|---|---|
| 5,392,789 A | * | 2/1995 | Slater | A61B 17/29 600/564 |
| 5,423,854 A | | 6/1995 | Martin et al. | |
| 6,840,938 B1 | * | 1/2005 | Morley | A61B 18/1445 606/50 |
| 8,568,443 B1 | * | 10/2013 | Jackman | A61B 17/00 606/157 |
| 8,858,588 B2 | * | 10/2014 | Sigmon, Jr. | A61B 17/10 606/205 |
| 2005/0049520 A1 | * | 3/2005 | Nakao | A61B 10/06 600/562 |
| 2009/0138006 A1 | | 5/2009 | Bales et al. | |
| 2010/0198253 A1 | * | 8/2010 | Jinno | A61B 17/29 606/205 |
| 2010/0298864 A1 | | 11/2010 | Castro | |
| 2011/0137337 A1 | * | 6/2011 | van den Dool | A61B 17/29 606/205 |
| 2011/0295251 A1 | | 12/2011 | Garrison | |
| 2012/0215234 A1 | | 8/2012 | Chowaniec et al. | |
| 2012/0259319 A1 | * | 10/2012 | Stefan | A61B 17/29 606/1 |

* cited by examiner

END EFFECTOR APPARATUS FOR A SURGICAL INSTRUMENT

CROSS-REFERENCE TO RELATED APPLICATION

This application is a U.S. National Phase Application under 35 U.S.C. 371 of International Application No. PCT/CA2016/000059 filed on Feb. 29, 2016 and published as WO 2016/165004 A1 on Oct. 20, 2016. This application is based on and claims the benefit of priority from U.S. Provisional Application No. 62/147,302, filed Apr. 14, 2015. The entire disclosures of all of the above applications are incorporated herein by reference.

BACKGROUND OF THE INVENTION

1. Field

This disclosure relates to apparatus used for surgical procedures and more particularly to an end effector for a robotic and/or laparoscopic surgical instrument.

2. Description of Related Art

Remotely actuated surgical instruments may be used in laparoscopic and/or robotic surgery applications where there is an area of limited access for an operator. The surgical instrument generally includes an end effector disposed at a distal end of a shaft and an actuator portion for manipulating the end effector at a proximate end of a shaft. The end effector and a portion of the surgical instrument inserted through an incision into a body cavity of a patient while the actuator portion generally remains outside the body cavity.

SUMMARY

In accordance with one disclosed aspect there is provided an end effector apparatus for a surgical instrument. The apparatus includes a first jaw mounted on a first revolute joint, the first jaw having a manipulating portion extending forwardly from the first revolute joint and a lever arm projecting rearwardly from the first revolute joint. The apparatus also includes a second jaw having a manipulating portion generally opposing the manipulating portion of the first jaw, and a coupler having an actuation end disposed overlapping the lever arm of the first jaw, the first and second jaws being laterally spaced apart to provide clearance for the actuation end of the coupler. The apparatus further includes a linkage extending rearwardly between the actuation end of the coupler and the lever arm of the first jaw, the linkage being operable to cause opening and closing movements of the first jaw about the first revolute joint in response to reciprocating movement of the coupler.

The coupler may be operably configured to cause an opening movement of the first jaw about the first revolute joint in response to forward movement of the actuation end of the coupler and to cause a closing movement of the first jaw about the first revolute joint in response to rearward movement of the actuation end of the coupler.

The rearward movement of the actuation end of the coupler increases an angle between the linkage and the coupler causing a corresponding increase in a component of force transmitted through the linkage for closing the first jaw providing increased leverage for maintaining the first jaw in a closed position.

The second jaw may be immovably mounted.

The second jaw may be mounted for movement on a second revolute joint, the second jaw having a lever arm projecting rearwardly from the second revolute joint and may further include a linkage extending rearwardly between the actuation end of the coupler and the lever arm of the second jaw, the linkage being operable to cause opening and closing movements of the second jaw about the second revolute joint in response to reciprocating movement of the actuation end of the coupler.

The actuating end of the coupler may include an opening for receiving a pivot pin for pivotally mounting to each of the linkages.

Each of the levers associated with the first and second jaws may include an opening for receiving a pivot pin for pivotally connecting the respective linkages to the respective levers.

The coupler may have an interface for receiving a control link, the control link being actuated by the surgical instrument for causing movement of the coupler.

The apparatus may include a housing operable to support the first and second revolute joints.

Each of the revolute joints may include a pivot pin supported within the housing and extending through an opening in the respective first and second jaws.

The housing may include an interface for removably mounting the end effector to a distal end of the surgical instrument.

Each pivot pin may be supported between a pair of electrically insulating bushings received in respective openings disposed on either side of the first jaw, the electrically insulated bushings being operable to electrically isolate the respective jaws from the housing.

Each of the first and second jaws may further include an electrical connection for connecting to respective electrical conductors associated with the surgical instrument, the electrical conductors being operable to supply an electrical current through the respective jaws.

The manipulating portion of at least one of the first and second jaws may include a cutting edge oriented toward the manipulating portion of the other of the first and second jaws for cutting tissue, a gripping surface oriented toward the manipulating portion of the other of the first and second jaws for grasping, and a retractor surface oriented away from the manipulating portion of the other of the first and second jaws for manipulating a retractable clamp.

The apparatus may include a housing surrounding at least the first revolute joint and the first revolute joint may include a pivot pin supported within the housing and extending through an opening in the first jaw.

The housing may include an interface for removably mounting the end effector to a distal end of the surgical instrument.

The pivot pin may be supported between a pair of electrically insulating bushings received in respective openings disposed on either side of the first jaw, the electrically insulated bushings being operable to electrically isolate the first jaw from the housing.

The first jaw may further include an electrical connection for connecting to an electrical conductor associated with the surgical instrument, the electrical conductor for supplying an electrical current through the first jaw.

In accordance with another disclosed aspect there is provided a method for actuating an end effector for a surgical instrument, the end effector including a first jaw mounted on a first revolute joint, the first jaw having a manipulating portion extending forwardly from the first revolute joint and a lever arm projecting rearwardly from the first revolute joint, a second jaw having a manipulating portion generally opposing the manipulating portion of the first jaw. The method involves causing reciprocating movement of a coupler having an actuation end disposed overlapping the lever arm of the first jaw, the first and second jaws being laterally spaced apart to provide clearance for the actuation end of the coupler, and transmitting reciprocating movements of the coupler through a linkage extending rearwardly between the actuation end of the coupler and the lever arm of the first jaw, the movement of the linkage being operable to cause opening and closing movements of the first jaw about the first revolute joint.

Other aspects and features of the present disclosure will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
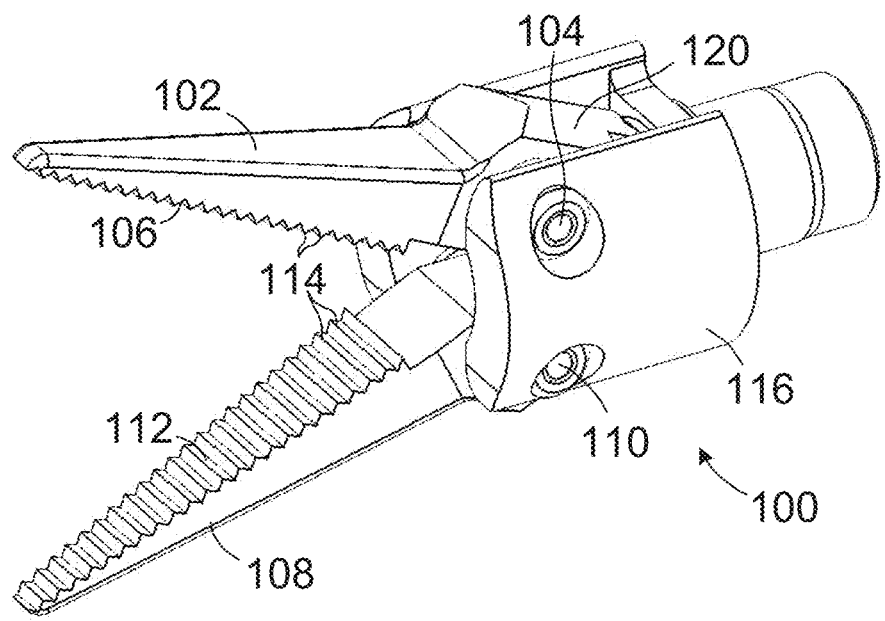
FIG. 1 is a perspective view of an end effector apparatus according to a first disclosed embodiment.

Referring to FIG. 1, an end effector apparatus according to a first embodiment of the invention is shown generally at 100. The end-effector 100 will generally be mounted to a surgical instrument (not shown in FIG. 1) for performing a surgical procedure. Several different surgical instruments and/or end effectors may be used for surgical tasks performed during a typical surgical procedure.

The end effector 100 includes a first jaw 102 mounted on a first revolute joint 104. The first jaw 102 has a manipulating portion 106 extending forwardly from the first revolute joint 104. The end-effector 100 also includes a second jaw 108, which in the embodiment shown is mounted on a second revolute joint 110. The second jaw 108 also has a manipulating portion 112 generally opposing the manipulating portion 106 of the first jaw 102. In the embodiment shown the manipulating portions 106 and 112 are each oriented toward each other and include a gripping surface comprising teeth 114 for grasping tissue, surgical sutures, suture needles, etc. In other embodiments one or both of the manipulating portions 106 and 112 may include a cutting edge for cutting tissue. Alternatively the manipulating portions 106 and 112 may include one or more retractor surfaces oriented away from the manipulating portion of the other of the first and second jaws for manipulating a retractable clamp. Various other types of manipulators may be implemented in place of the manipulating portions 106 and 112 shown in FIG. 1.

Figure 2:
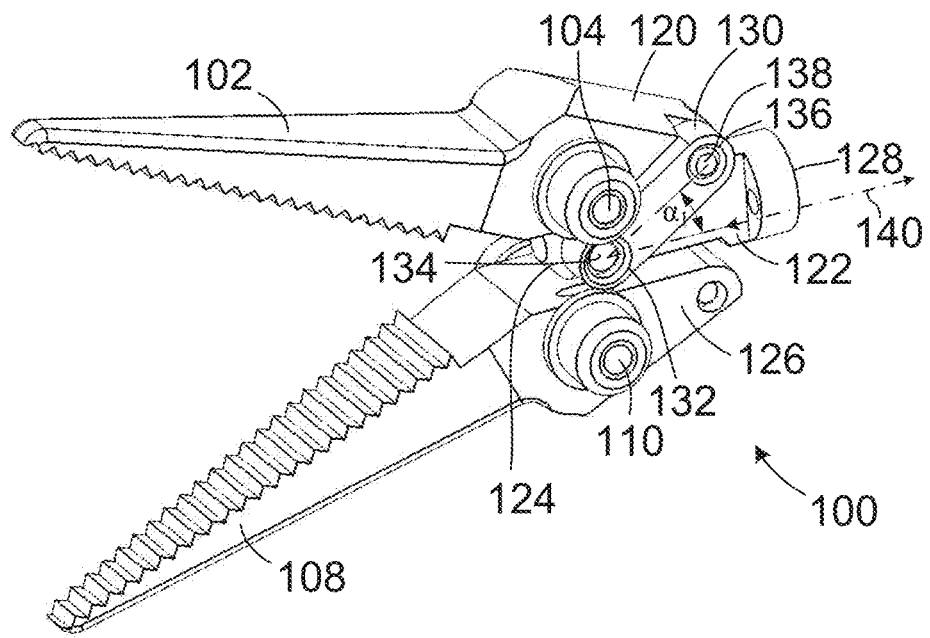
FIG. 2 is a perspective view of the end effector apparatus of FIG. 1 with a housing portion removed.

In the embodiment shown in FIG. 1, the end-effector 100 includes a housing 116 and the first and second revolute joints 104 and 110 are supported within the housing. The first jaw 102 further includes a lever arm 120 (partially obscured by the housing 116) projecting rearwardly from the first revolute joint 104. Referring to FIG. 2, the end-effector 100 is shown with the housing 116 removed in FIG. 2 to reveal the lever arm 120. The end-effector 100 further includes a coupler 122 having a forwardly oriented actuation end 124 and rearwardly oriented interface end 128. The interface end 128 is configured for connecting to control links of a surgical instrument as will be described later herein. The actuation end 124 is disposed overlapping the lever arm 120 of the first jaw 102. The second jaw 108 also includes a lever arm 126 projecting rearwardly from the second revolute joint 110 and the first and second jaws 102 and 108 are laterally spaced apart to provide clearance for the actuation end 124 of the coupler 122 between the jaws.

The end-effector 100 further includes a linkage 130 extending generally rearwardly from the actuation end 124 of the coupler 122 to the lever arm 120 of the first jaw 102. In this embodiment the linkage 130 includes an opening 132 for receiving a pivot pin 134 that extends through the actuation end 124 of the coupler 122. The linkage 130 also includes an opening 136 for receiving a pivot pin 138 that extends through a corresponding opening (not shown) in the lever arm 120. The pivot pins 134 and 138 facilitate movement of the linkage 130 about the pivot pins and the linkage is operable to cause opening and closing movements of the first jaw 102 about the first revolute joint 104 in response to reciprocating movement of the coupler 122 in a direction generally aligned with the arrow 140.

Figure 3:
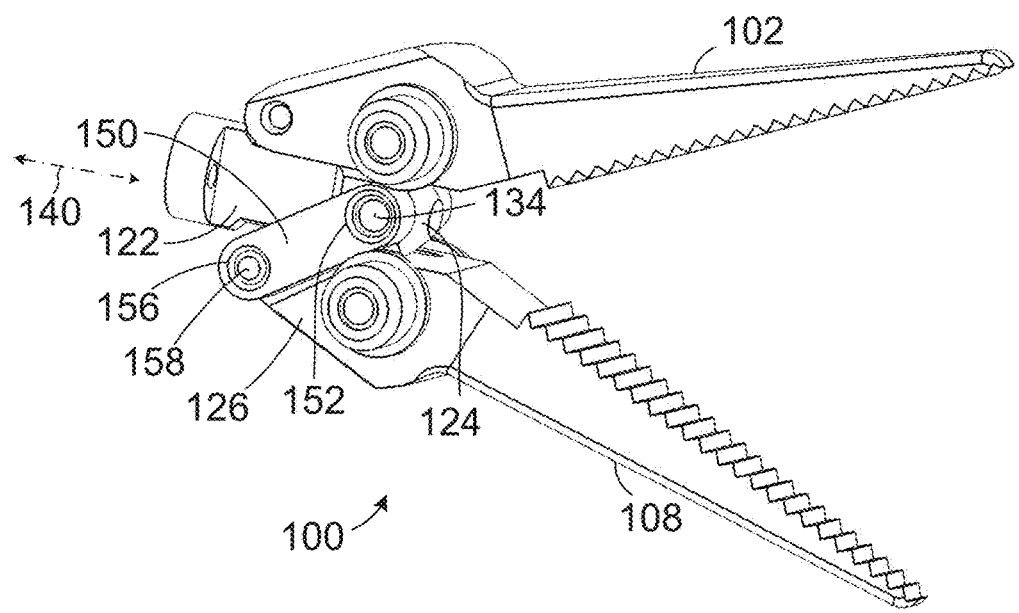
FIG. 3 is a perspective view of an opposite side of the end effector apparatus shown in FIG. 2.

The end-effector 100 also includes a linkage associated with movement of the second jaw 108 located on the opposite side of the end effector (not visible in FIG. 2). An opposite side of the end-effector 100 is shown in FIG. 3. Referring to FIG. 3, the end effector 100 also includes a linkage 150 extending generally rearwardly from the actuation end 124 of the coupler 122 to the lever arm 126 of the second jaw 108. The linkage 150 includes an opening 152 for receiving the pivot pin 134 extending through the actuation end 124 of the coupler 122. In this embodiment the pivot pin 134 is common to both linkages 130 and 150. The linkage 150 further includes an opening 156 for receiving a pivot pin 158 that extends through a corresponding opening (not shown) in the lever arm 126. The pivot pins 134 and 158 facilitate movement of the linkage 150 about the pivot pins and the linkage is operable to cause opening and closing movements of the second jaw 108 about the second revolute joint 110 in response to the reciprocating movement of the coupler 122 in the direction 140.

Figure 4:
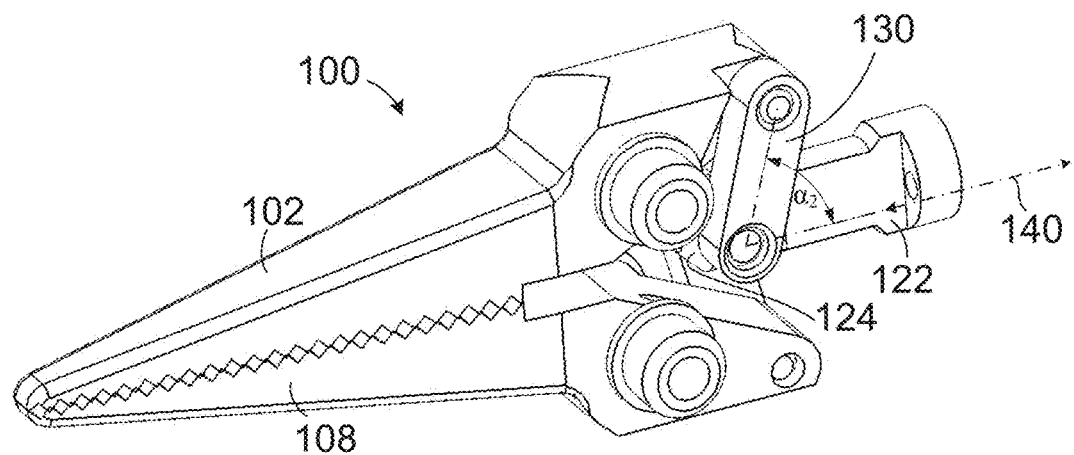
FIG. 4 is a perspective view of the end effector shown in FIG. 2 in a closed state.
Figure 5:
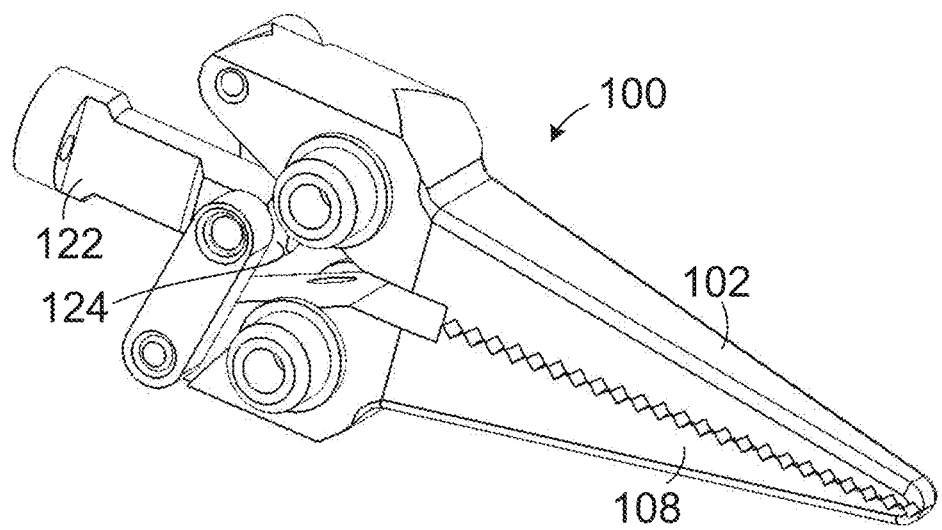
FIG. 5 is a perspective view of an opposite side of the end effector apparatus shown in FIG. 3.

Referring back to FIG. 2, the first and second jaws 102 and 108 are shown in an open state, caused by the actuation end 124 of the coupler 122 being disposed forwardly with respect to the jaws. Under these conditions, the first jaw 102 has been rotated to open about the first revolute joint 104 and the second jaw 108 has been rotated to open about the second revolute joint 110. Referring to FIG. 4 and FIG. 5, the first and second jaws 102 and 108 are shown in a closed state caused by the actuation end 124 of the coupler 122 having been moved rearwardly with respect to the jaws. Under these conditions, the first jaw 102 has been rotated to close about the first revolute joint 104 and the second jaw 108 has been rotated to close about the second revolute joint 110. The coupler 122 is operable to cause the opening movement of the first jaw 102 about the first revolute joint 104 in response to receiving a forwardly directed force at the interface end 128 and to cause a closing movement of the first jaw about the first revolute joint in response to receiving a rearwardly directed force at the interface end of the coupler.

The configuration of the linkages 130 and 150 shown advantageously provides a greater force closing the jaws 102 and 108 than when opening the jaws. In the closed state of the jaws 102 and 108 shown in FIG. 4, an angle $\alpha_2$ between the coupler movement direction 140 and the linkage 130 is greater than the angle $\alpha_1$ in the open state (shown in FIG. 2). For a similar actuation force exerted on the forwardly oriented actuation end 124 and rearwardly oriented interface end 128 of the coupler 122, a tension component of the actuation force in the linkage 130 when opening is significantly reduced over a compression component of the actuation force in the linkage when closing, due to the angle $\alpha_2$ being larger than the angle $\alpha_1$. Thus, rearward movement of the actuation end 124 of the coupler 122 increases the angle $\alpha$ between the linkage 130 and the coupler causing a corresponding increase in the component of force transmitted through the linkage for closing the first jaw. The same effect also occurs in connection with the linkage 150 associated with the second jaw 108, thus providing increased leverage for grasping and maintaining the jaws in a closed position.

The overlapping of the actuation end 124 of the coupler 122 with the first jaw 102 and the linkage 130 extending rearwardly between the actuation end and the lever arm 120 has the advantage of shortening the overall length of the end effector 100. This may be useful in some surgical systems where the end-effector is connected to a surgical instrument that has a dexterous shaft. For example, the surgical instrument may be configured as an articulated tool positioner as described in detail in commonly owned patent applications PCT/CA2013/001076 entitled "ARTICULATED TOOL POSITIONER AND SYSTEM EMPLOYING SAME" and PCT/CA2015/000098 entitled "ACTUATOR AND DRIVE FOR MANIPULATING A TOOL" filed on Feb. 18, 2015. The articulated tool positioner disclosed in these applications permits dexterous movement of an end effector such as the end effector 100. However dexterous manipulation of the end effector itself is not possible, since the jaws and housing are rigid and thus a shortened end effector provides for better access and maneuverability during surgical operations.

Figure 6:
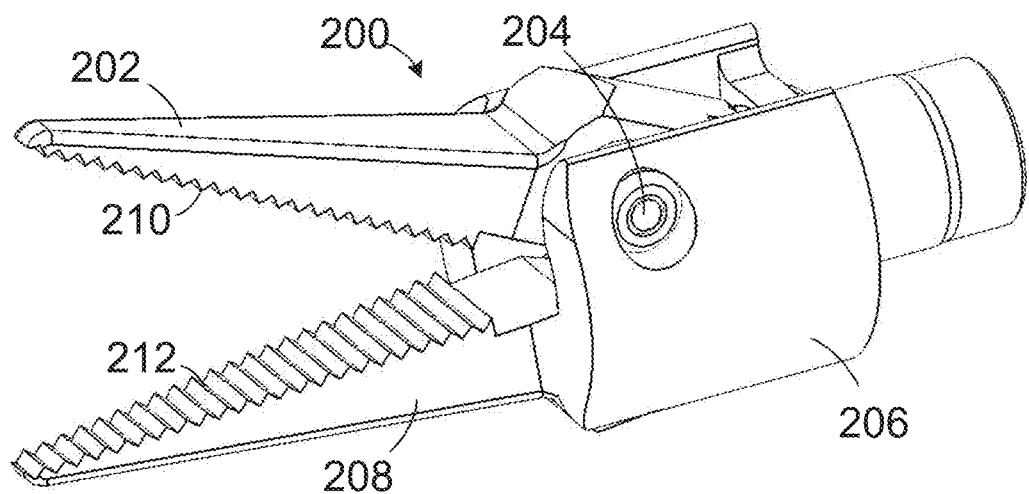
FIG. 6 is a perspective view of an end effector apparatus according to an alternative disclosed embodiment.

Referring to FIG. 6, an alternative embodiment of the end effector shown generally at 200. In this embodiment the end effector 200 includes a first jaw 202 mounted for movement on a revolute joint 204 supported with a housing 206 as generally described in connection with the first jaw 102. The end effector 200 also includes a second jaw 208. However in thus embodiment the second jaw 208 is immovably mounted within the housing 116 and the end effector thus provides for a single ended movement of the first jaw 202 with respect to the second jaw 208. In this embodiment the second jaw is formed integrally with the housing 206, although in other embodiments the second jaw may be fabricated separately from the housing and otherwise immovably supported. As in the case of the embodiments shown in FIG. 1-5 the jaws 202 and 208 each include gripper surfaces 210 and 212, but in other embodiments at least one of the jaws may be configured for cutting, retracting, or other functions.

Figure 7:
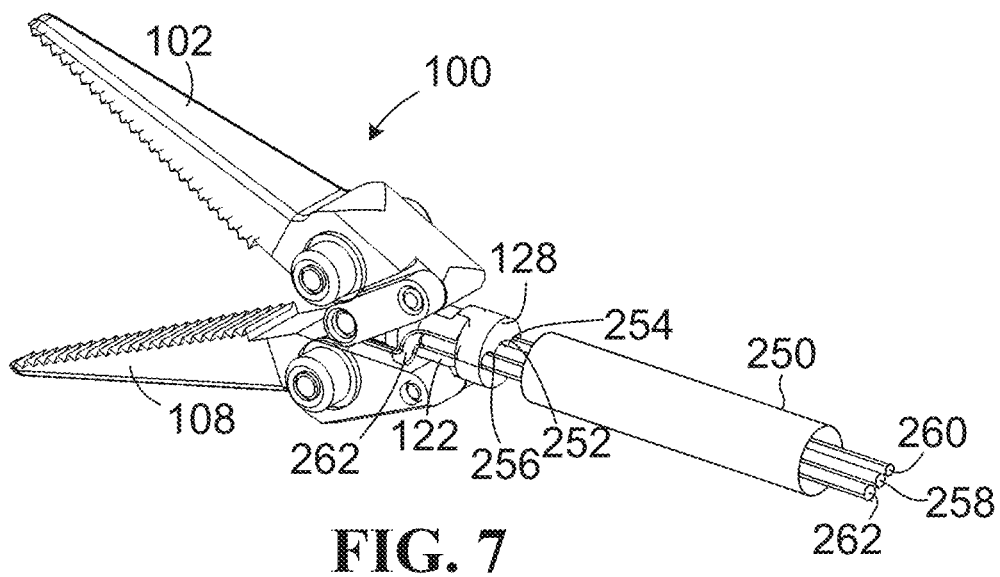
FIG. 7 is a rear perspective view of the end effector shown in FIG. 2 mounted to a portion of a surgical instrument.

Referring to FIG. 7, the end effector 100 is shown in rear perspective view along with a portion of an outer sheath 250 associated with a surgical instrument (not shown) to which the end effector is connected for operating the end effector 100. The interface end 128 of the coupler 122 has openings 252, 254, and 256 for receiving one or more controls associated with the surgical instrument. In this embodiment the controls extend though the outer sheath 250 and include a control link 258 for causing the reciprocating movement of the coupler 122 and a pair of electrical conductors 260 and 262 for providing electrical current to the jaws 102 and 108 as described later herein. In one embodiment the control link 258 may be a rod or a flexible wire such as nitinol that is capable of transmitting both tension and compression forces. The control link 258 is received in the opening 254 and may be secured to the coupler by a welding process such as laser welding or may be soldered, crimped, or otherwise connected.

Figure 8:
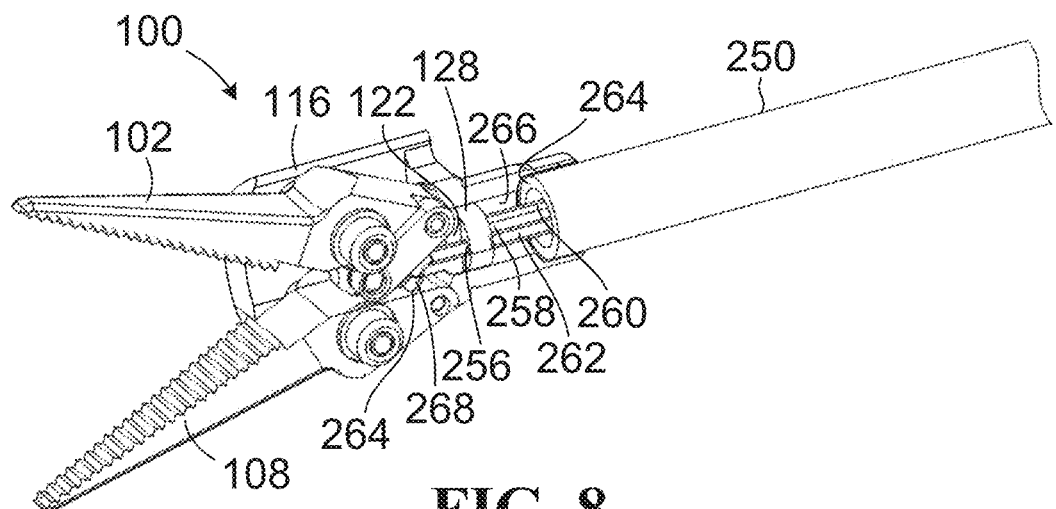
FIG. 8 is a rear perspective view of the end effector shown in FIG. 7.

Referring to FIG. 8, the end-effector 100 is shown together with a portion of the housing 116, the remainder of which has been cut away to show the underlying portions of the end effector. The outer sheath 250 of the surgical instrument is received in the housing 116. In the state shown where the coupler 122 is disposed in a forward position for opening the jaws 102 and 108, the interface end 128 of the coupler 122 is longitudinally spaced apart from an end 264 of the outer sheath 250 to permit rearward movement of the coupler for closing the jaws. The coupler 122 is accommodated in a cylindrical channel 266 that is sized to provide for free reciprocating movement of the coupler for operating the jaws 102 and 108.

Still referring to FIG. 8, the electrical conductor 262 is insulated and extends through the opening 256 in the interface end 128 of the coupler 122. The opening 256 is sized to permit free reciprocating movement of the coupler 122 without being impeded by the electrical conductor 262. The second jaw 108 further includes an opening 268 for receiving an end 270 of the electrical conductor 262 from which the insulation has been removed. The end 270 of the electrical conductor 262 makes an electrical connection to the second jaw 108 via the opening 268 and may be crimped or soldered, for example. Similarly the electrical conductor 260 is also insulated and extends through the opening 254 which is also sized to permit free reciprocating movement of the coupler 122 without being impeded by the electrical conductor 260. The first jaw 102 also includes an opening for receiving an end of the electrical conductor 260 from which the insulation has been removed (not visible in FIG. 8). The electrical conductor 260 thus also makes electrical connection to the first jaw 102 as shown for the second jaw 108.

Figure 9:
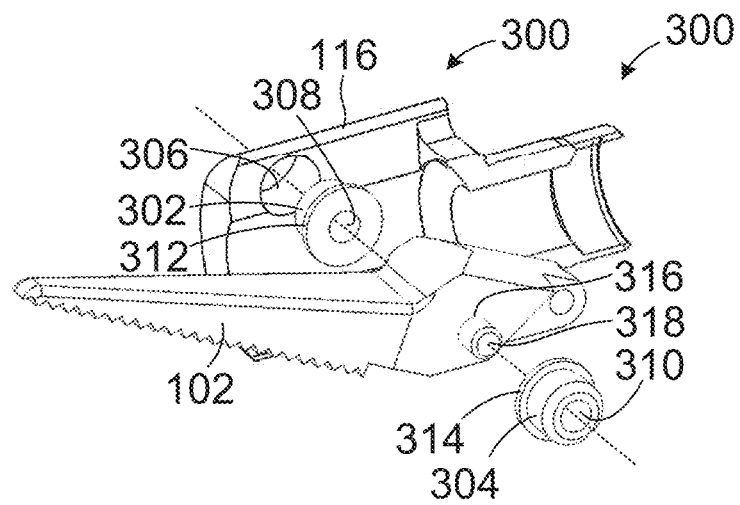
FIG. 9 is an exploded view of a revolute joint and a portion of the housing of the end effector shown in FIG. 1.

Referring to FIG. 9, an exploded view of the first revolute joint 104 and a portion of the housing 116 is shown generally at 300. In the embodiment shown the housing 116 and first jaw 102 are both fabricated from an electrically conductive material such as stainless steel. The first revolute joint 104 includes a first electrically insulated bushing 302 and a second electrically insulated bushing 304. The housing 116 includes an opening 306 for receiving the first bushing 302. Similarly, a portion of the housing 116 not shown in FIG. 9 includes an opening for receiving the second bushing 304. The first jaw 102 includes an opening 316 extending through the jaw, and the first revolute joint 104 further includes a pivot pin 318. Each of the bushings 302 and 304 includes a respective opening 308 and 310 for receiving the pivot pin 318. The bushings 302 and 304 also include respective flanges 312 and 314, disposed facing respective sides of the first jaw 102. When assembled, the bushings 302 and 304 insulate between the housing 116 and the first jaw 102. The flanges 312 and 314 act as insulating washers that space the first jaw 102 away from the housing 116 on both sides so that portions of the jaw do not contact the housing during operation. The pivot pin 318 may also be conductive, but is electrically insulted from the housing 116 by the bushings 302 and 304. The second revolute joint 110 of the second jaw 108 is similarly configured such that each of the jaws is electrically isolated from the housing 116. The first jaw 102 and second jaw 108 are also electrically isolated from each other when open. An electrical current received from the surgical instrument through the electrical conductor 260 flows through the first jaw 102, through any tissue being grasped between the jaws, and through the second jaw 108 and electrical conductor 262 to complete the electrical circuit. The current may be selectively controlled by a surgeon operating the surgical instrument for electro-cauterization of tissue during a surgical procedure.

In the disclosed embodiments the configuration of the coupler 122 and the linkages 130 and 150 provides for both increased leverage when closing the jaws 102 and 108 and shortens the overall length of the end effector.

While specific embodiments of the invention have been described and illustrated, such embodiments should be considered illustrative of the invention only and not as limiting the invention as construed in accordance with the accompanying claims.

What is claimed is:

1. An end effector apparatus for a surgical instrument, the apparatus comprising:
    a first jaw being mounted on a first revolute joint, the first jaw having:
        a manipulating portion extending forwardly from the first revolute joint, and
        a lever arm projecting rearwardly from the first revolute joint;
    a second jaw being mounted on a second revolute joint, the second jaw having a manipulating portion generally opposing the manipulating portion of the first jaw;
    a coupler having an actuation end disposed overlapping the lever arm of the first jaw, the first revolute joint and the second revolute joint being laterally spaced apart to provide a clearance for the actuation end of the coupler such that the clearance is configured to receive a distalmost end of the actuation end and
    a first linkage extending rearwardly between the actuation end of the coupler and the lever arm of the first jaw, the first linkage being operable to cause opening and closing movements of the first jaw about the first revolute joint in response to reciprocating movement of the coupler, the first linkage being pivotally connected to the coupler by a first pivot pin and pivotally connected to the lever arm by a second pin, wherein a first linkage length is defined between the first pivot pin and the second pivot pin, and wherein a first arm length is defined between the first revolute joint and the second pivot pin,
        wherein the first arm length and the first linkage length are selected such that:
            the distalmost end of the actuation end is positioned distal to a proximal end of the first revolute joint and between the first revolute joint and the second revolute joint and is within the clearance when the end effector apparatus is in an open state; and
            the distalmost end of the actuation end is positioned rearwardly of the first revolute joint and the clearance when the end effector apparatus is in a closed state.

2. The apparatus of claim 1 wherein the coupler is operably configured to cause an opening movement of the first jaw about the first revolute joint in response to forward movement of the actuation end of the coupler into the clearance between the first and second revolute joints and to cause a closing movement of the first jaw about the first revolute joint in response to rearward movement of the actuation end of the coupler.

3. The apparatus of claim 2 wherein the rearward movement of the actuation end of the coupler increases an angle between the first linkage and the coupler causing a corresponding increase in a component of force transmitted through the first linkage for closing the first jaw providing increased leverage for maintaining the first jaw in a closed position.

4. The apparatus of claim 1 wherein the second jaw the second jaw has a lever arm projecting rearwardly from the second revolute joint, and wherein the apparatus further comprises:
    a second linkage extending rearwardly between the actuation end of the coupler and the lever arm of the second jaw, the second linkage being operable to cause opening and closing movements of the second jaw about the second revolute joint in response to reciprocating movement of the actuation end of the coupler.

5. The apparatus of claim 4 wherein the actuating end of the coupler comprises an opening for receiving the first pivot pin and a second pivot pin for pivotally mounting to each of the first and second linkages.

6. The apparatus of claim 4 wherein each of the lever arms associated with the first and second jaws comprises an opening for receiving the first pivot pin and a second pivot pin for pivotally connecting the respective linkages to the respective lever arms.

7. The apparatus of claim 4 wherein the coupler has an interface for receiving a control link, the control link being actuated by the surgical instrument for causing movement of the coupler.

8. The apparatus of claim 4 further comprising a housing operable to support the first and second revolute joints.

9. The apparatus of claim 8 wherein the first revolute joint comprises a first revolute pivot pin and the second revolute joint comprises a second revolute pivot pin, the first and second revolute pivot pins supported within the housing and extending through an opening in the respective first and second jaws.

10. The apparatus of claim 8 wherein the housing comprises an interface for removably mounting the end effector to a distal end of the surgical instrument.

11. The apparatus of claim 9 wherein each of the first and second revolute pivot pins is supported between a pair of electrically insulating bushings received in respective openings disposed on either side of the first jaw, the electrically insulated bushings being operable to electrically isolate the respective jaws from the housing.

12. The apparatus of claim 11 wherein each of the first and second jaws further comprise an electrical connection for connecting to respective electrical conductors associated with the surgical instrument, the electrical conductors being operable to supply an electrical current through the respective jaws.

13. The apparatus of claim 1 wherein at least one of the manipulating portion of the first jaw and the manipulating portion of the second jaw comprises:
    a cutting edge oriented toward the manipulating portion of the other of the first and second jaws for cutting tissue;

a gripping surface oriented toward the manipulating portion of the other of the first and second jaws for grasping; and a retractor surface oriented away from the manipulating portion of the other of the first and second jaws for manipulating a retractable clamp.

14. The apparatus of claim 1 further comprising a housing surrounding at least the first revolute joint, wherein the first revolute joint comprises a revolute pivot pin supported within the housing and extending through an opening in the first jaw.

15. The apparatus of claim 14 wherein the housing comprises an interface for removably mounting the end effector to a distal end of the surgical instrument.

16. The apparatus of claim 14 wherein the revolute pivot pin is supported between a pair of electrically insulating bushings received in respective openings disposed on either side of the first jaw, the electrically insulated bushings being operable to electrically isolate the first jaw from the housing.

17. The apparatus of claim 16 wherein the first jaw further comprises an electrical connection for connecting to an electrical conductor associated with the surgical instrument, the electrical conductor for supplying an electrical current to the first jaw.

18. A method for actuating an end effector for a surgical instrument, the end effector including a first jaw being mounted on a first revolute joint, the first jaw having a manipulating portion extending forwardly from the first revolute joint and a lever arm projecting rearwardly from the first revolute joint, a second jaw being mounted on a second revolute joint and having a manipulating portion generally opposing the manipulating portion of the first jaw, the method comprising:

causing reciprocating movement of a coupler having an actuation end disposed overlapping the lever arm of the first jaw, the first revolute joint and the second revolute joint being laterally spaced apart to provide a clearance for the actuation end of the coupler such that the clearance is configured to receive a distalmost end of the actuation end, transmitting reciprocating movements of the coupler through a linkage extending rearwardly between the actuation end of the coupler and the lever arm of the first jaw, the movement of the linkage being operable to cause opening and closing movements of the first jaw about the first revolute joint, the first linkage being pivotally connected to the coupler by a first pivot pin and pivotally connected to the lever arm by a second pin, wherein a first linkage length is defined between the first pivot pin and the second pivot pin, and wherein a first arm length is defined between the first revolute joint and the second pivot pin, wherein the first arm length and the first linkage length are selected such that:

the distalmost end of the actuation end is positioned distal to a proximal end of the first revolute joint and between the first revolute joint and the second revolute joint and is within the clearance when the end effector apparatus is in an open state; and the distalmost end of the actuation end is positioned rearwardly of the first revolute joint and the clearance when the end effector apparatus is in a closed state.

19. The method of claim 18 wherein causing reciprocating movements of the coupler comprises causing reciprocating movement of the coupler in a distal direction towards the first revolute joint and the clearance to transition the end effector to the open state such that the distalmost end of the actuation end is positioned distal to the proximal end of the first revolute joint and is positioned within the clearance.

20. The method of claim 18 wherein causing reciprocating movements of the coupler comprises causing reciprocating movement of the coupler in a proximal direction away from the first revolute joint and the clearance to transition the end effector to the close state such that the distalmost end of the actuation end is positioned rearwardly of the first revolute joint, the second revolute joint, and the clearance.

* * * * *